US010507272B2

(12) United States Patent
Lee et al.

(10) Patent No.: US 10,507,272 B2
(45) Date of Patent: Dec. 17, 2019

(54) WEARABLE VAD CONTROLLER WITH RESERVE BATTERY

(71) Applicant: WorldHeart, Inc., Miami Lakes, FL (US)

(72) Inventors: Jim Lee, Benicia, CA (US); James Malmstrom, Kaysville, UT (US); James Long, Salt Lake City, UT (US)

(73) Assignee: WorldHeart, Inc., Miami Lakes, FL (US)

( * ) Notice: Subject to any disclaimer, the term of this patent is extended or adjusted under 35 U.S.C. 154(b) by 0 days.

(21) Appl. No.: 15/969,059

(22) Filed: May 2, 2018

(65) Prior Publication Data

US 2018/0243493 A1 Aug. 30, 2018

Related U.S. Application Data

(62) Division of application No. 12/602,914, filed as application No. PCT/US2008/066126 on Jun. 6, 2008, now Pat. No. 9,993,588.

(Continued)

(51) Int. Cl.
*A61M 1/10* (2006.01)
*A61M 1/12* (2006.01)

(52) U.S. Cl.
CPC .............. *A61M 1/122* (2014.02); *A61M 1/12* (2013.01); *A61M 1/127* (2013.01); *A61M 2205/8206* (2013.01)

(58) Field of Classification Search
CPC ..................................................... A61M 1/10
See application file for complete search history.

(56) References Cited

U.S. PATENT DOCUMENTS 4,376,312 A 3/1983 Robinson et al.
4,665,896 A 5/1987 LaForge et al.
(Continued)

FOREIGN PATENT DOCUMENTS

JP 1993060112 8/1993
JP H10432991 A 2/1998
(Continued)

OTHER PUBLICATIONS

Extend European Search Report dated Jan. 22, 2014, in EP Patent Application No. 08770343.5.
(Continued)

*Primary Examiner* — Matthew W Schall
(74) *Attorney, Agent, or Firm* — Christopher & Weisberg, P.A.

(57) ABSTRACT

There is disclosed apparatus and methods for providing a reserve power source for a ventricular assist device. In an embodiment, the apparatus includes a primary power source for powering the device, and a controller housing having a reserve battery for powering the device when the primary power source provides inadequate power, and the controller housing configured for use externally of the patient with a percutaneous cable to the device. In another embodiment, a method includes powering the device with a primary power source, monitoring power provided to the device, powering the device when the power is monitored as inadequate to the device with a reserve power source disposed within a controller housing, the device disposed subcutaneously within a patient, the controller housing disposed externally of the patient, and the device and the controller housing connected by a percutaneous cable. Other embodiments are also disclosed.

7 Claims, 2 Drawing Sheets

Related U.S. Application Data

(60) Provisional application No. 60/933,607, filed on Jun. 6, 2007.

(56) References Cited

U.S. PATENT DOCUMENTS

| | | | |
|---|---|---|---|
| 4,666,443 | A | 5/1987 | Portner |
| 5,569,156 | A | 10/1996 | Mussivand |
| 5,704,891 | A | 1/1998 | Mussivand |
| 5,766,207 | A * | 6/1998 | Potter .................. A61M 1/106 600/16 |
| 5,810,758 | A | 9/1998 | Yamazaki et al. |
| 6,123,726 | A | 9/2000 | Mori et al. |
| 6,132,363 | A | 10/2000 | Freed et al. |
| 6,605,032 | B2 | 8/2003 | Benkowski et al. |
| 2003/0069465 | A1 | 4/2003 | Benkowski et al. |
| 2004/0097782 | A1 | 5/2004 | Korakianitis et al. |
| 2007/0197854 | A1 | 8/2007 | Maarseille et al. |

FOREIGN PATENT DOCUMENTS

| | | |
|---|---|---|
| JP | H10085322 A | 4/1998 |
| JP | H10127758 A | 5/1998 |
| JP | 2002505919 A | 2/2002 |
| JP | 2002540856 A | 12/2002 |
| JP | 2005236085 A | 9/2005 |
| JP | 2006514842 A | 5/2006 |
| WO | 99/45981 A1 | 9/1999 |
| WO | 00/59560 A1 | 10/2000 |
| WO | 2004/017831 A1 | 3/2004 |
| WO | 2007053881 A1 | 5/2007 |

OTHER PUBLICATIONS

El-Banayosy, et al., "The European Experience of Novacor Left Ventricular Assist (LVAS) Therapy as a Bridge to Transplant: A Retrospective Multi-Centre Study" Eur. J. Cardio—Thoracic Surgery: vol. p. 835-841 (1999).

* cited by examiner

WEARABLE VAD CONTROLLER WITH RESERVE BATTERY

REFERENCE TO PENDING PRIOR PATENT APPLICATION

This application is a divisional of U.S. patent application Ser. No. 12/602,914, filed May 24, 2010, which application is National Stage Entry of Application Serial No. PCT/US08/66126, filed Jun. 6, 2008, which application is related to and claims priority from Provisional Application Ser. No. 60/933,607, filed Jun. 6, 2007, the entirety of all of which are incorporated herein by reference.

BACKGROUND

Ventricular assist devices (VAD) pump blood in parallel with the native ventricles of the human heart. This provides blood flow to the body when the patient's own heart is in failure. A typical implantation of a VAD in the left side configuration takes blood from the apex of the left ventricle and returns blood to the ascending aorta at higher pressure. The VAD thereby takes on a significant portion of the work done by the native heart without removing the native heart.

VADs are at times used in temporary applications, such as bridge to heart transplantation or bridge to recovery of the native heart. However, the largest application of VAD's is likely to be long-term use of the device through the duration of the patient's life. This is also known as destination therapy (DT) use of the device.

There are several commercially available VAD systems that use batteries to power the controller and pump. These include the Thoratec HEARTMATE I® and HEARTMATE II®, from Thermedics, Inc. the WorldHeart Novacor® system, from WorldHeart Corporation, and others. Generally, these systems are required to have two sources of power to be able to operate safely. Previous systems have been implemented with two external batteries, or one external battery and a power supply from the AC mains that must be connected to the patient and all times.

Totally implantable systems have been developed to the research or commercialization stage that include a bridge battery and an external power source supplied through a transcutaneous energy system. These systems include Implantable heart assistance devices from ARROW LION-HEART™, from Penn State College of Medicine, the Jarvik 2000 ®, from Jarvik, and the Abiomed AbioCor® Total Artificial Heart, from Abiomed, Inc. None of these systems apply the reserve battery concept to an externally wearable controller.

SUMMARY OF THE INVENTION

In an embodiment, there is provided an apparatus for providing a reserve power source for a ventricular assist device, the apparatus comprising a primary power source for powering the ventricular assist device disposed subcutaneously within a patient; and a controller housing having a reserve battery therein for powering the ventricular assist device when the primary power source provides inadequate power to the ventricular assist device, and the controller housing configured for use externally of the patient with a percutaneous cable to the ventricular assist device.

In another embodiment, there is provided a method of providing a reserve power source for a ventricular assist device, the method comprising powering the ventricular assist device with a primary power source; monitoring power provided to the ventricular assist device by the primary power source; and powering the ventricular assist device when the power is monitored as inadequate to the ventricular assist device with a reserve power source disposed within a controller housing, the ventricular assist device disposed subcutaneously within a patient, the controller housing disposed externally of the patient, and the ventricular assist device and the controller housing connected by a percutaneous cable.

In yet another embodiment, there is provided apparatus for providing a reserve power source for a mechanical circulatory support device, the apparatus comprising a primary power source for powering the mechanical circulatory support device disposed subcutaneously within a patient; and a controller housing having a reserve battery therein for powering the mechanical circulatory support device when the primary power source provides inadequate power to the mechanical circulatory support device, and the controller housing configured for use externally of the patient with a percutaneous cable to the mechanical circulatory support device.

In still another embodiment, there is provided a method of providing a reserve power source for a mechanical circulatory support device, the method comprising powering the mechanical circulatory support device with a primary power source; monitoring power provided to the mechanical circulatory support device by the primary power source; and powering the mechanical circulatory support device when the power is monitored as inadequate to the mechanical circulatory support device with a reserve power source disposed within a controller housing, the mechanical circulatory support device disposed subcutaneously within a patient, the controller housing disposed externally of the patient, and the mechanical circulatory support device and the controller housing connected by a percutaneous cable.

Other embodiments are also disclosed.

BRIEF DESCRIPTION OF THE DRAWINGS

Illustrative embodiments of the invention are illustrated in the drawings, in which.

DETAILED DESCRIPTION

In various embodiments, methods and apparatus are disclosed for providing a reserve power source for a ventricular assist device (or a mechanical circulatory support device). The reserve power source may be provided within a controller housing so as to provide enhanced device for managing the care of VAD patients.

Electric ventricular assist devices have typically required an external source of power, such as a battery when the patient is mobile, or connection to the AC mains power when the patient is sleeping or otherwise stationary. Typically, an electronic controller is required to control the pumping apparatus, and to modulate the delivery of the external power to the pumping apparatus. In such a system, the controller may be external to the body. Generally, at least two sources of power are required to operate the system in a safe manner. If the first power source fails or becomes discharge, then the pump continues to run seamlessly on the second power source. Previous VAD systems have used two external batteries or an external battery with a connection to the AC mains to provide redundancy required for safe operation.

Figure 1:
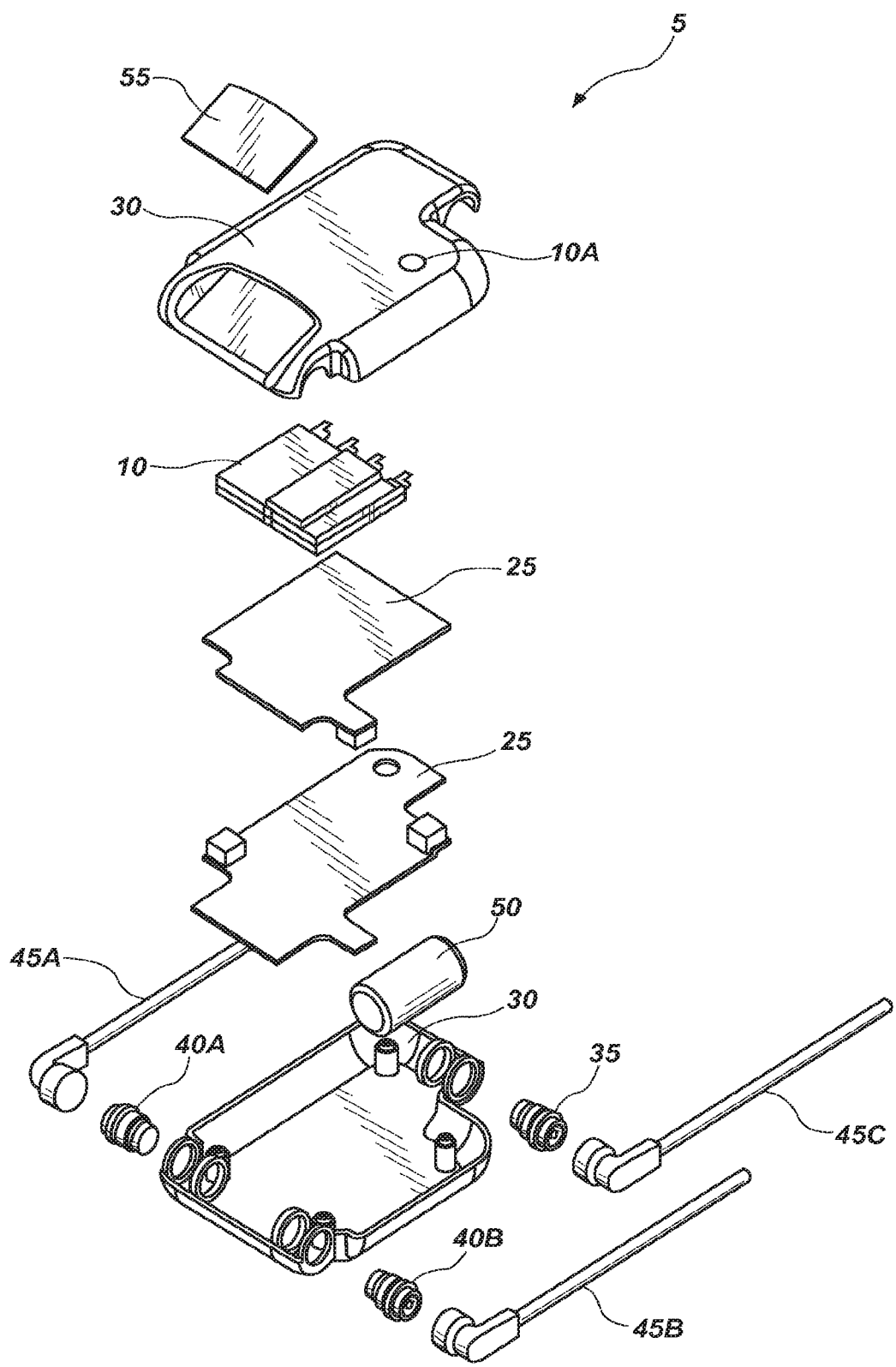
FIG. 1 illustrates an exploded view of an exemplary controller with a reserve battery.
Figure 2:
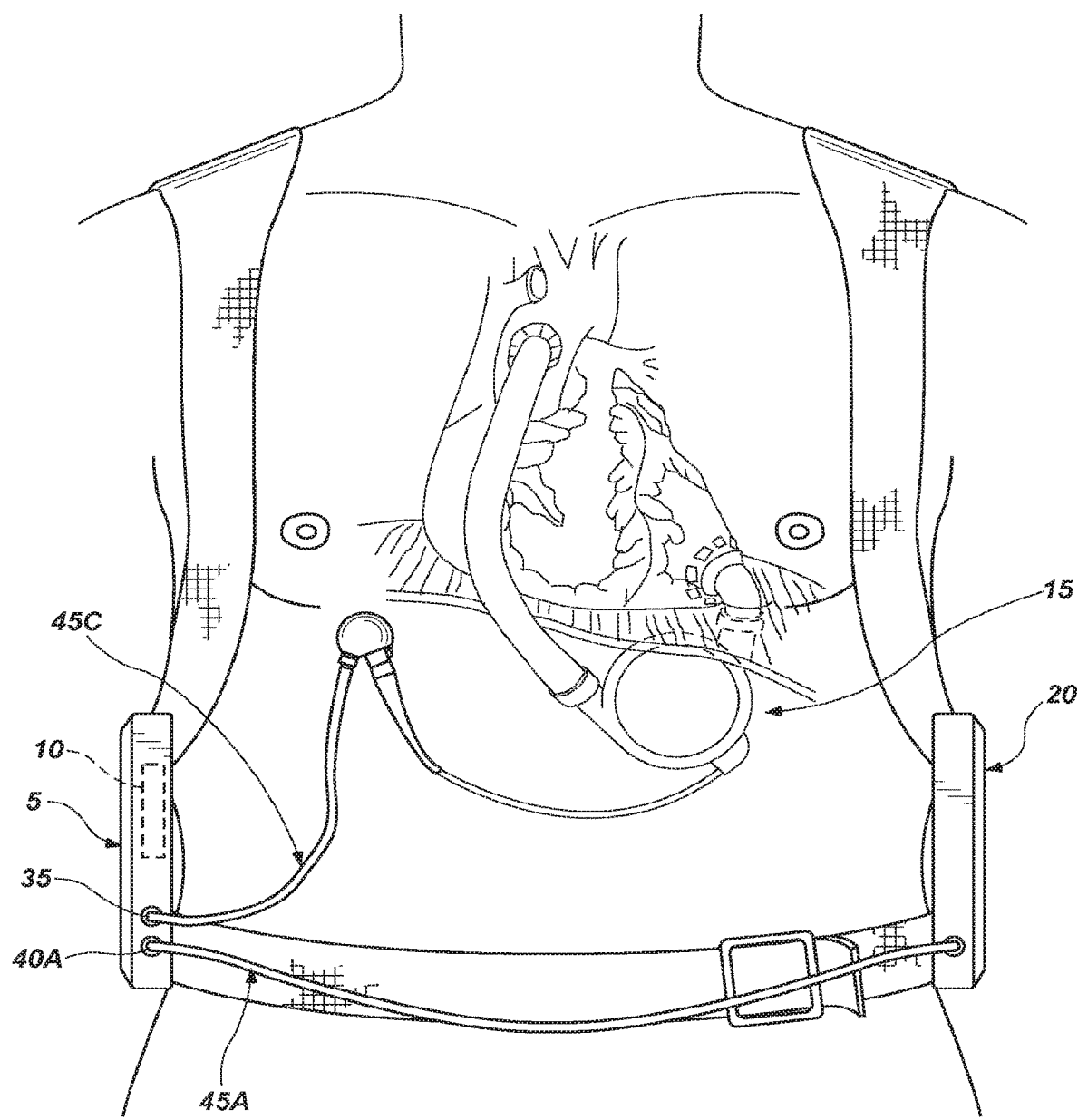
FIG. 2 illustrates a diagrammatic view of the exemplary controller of FIG. 1 in use by a patient.

Referring to FIGS. 1 and 2, and in exemplary embodiments, an external controller 5 may include a reserve battery 10 to provide a redundant power supply to a ventricular assist device or other type of mechanical circulatory support device, which are collectively referred to herein below as a pump 15 or pump system 15. In an embodiment, reserve battery 10 to operate pump system 15 is within controller 5. This configuration allows a patient to manage only two "external packages," instead of three external packages. The two "packages" may include external controller 5 and one external battery 20 (FIG. 2) or external controller 5 and a connection to AC mains. (For example, an external power connection 45B may provide AC mains to controller 5.) Previously, a patient was required for safety reasons to manage a controller and two external power sources, such as two external batteries 20 or an external battery 20 together with a separate connection to AC mains. (Not shown separate from controller 5).

FIG. 1 shows an exemplary embodiment of controller 5 having a reserve battery 10. In FIG. 1, there is shown reserve battery 10, which may be a rechargeable battery or another suitable battery, within the controller housing 5 that operates VAD pumping system 15 to continue to deliver blood when there is no external power applied to the controller 5, such as from external battery 20.

Referring still to FIG. 1, at least one printed circuit board 25 may be provided within housing components 30 of controller 5. The one or more printed circuit bards 25 may be configured to control pump system 15. The one or more printed circuit boards 25 may be configured to monitor the power supply received from either an external battery through port 40A of external power connection 45A or an AC mains source through port 40B of external power connection 45B. The one or more printed circuit boards 25 may be configured to monitor the power supply through port 35 of external power connection 45C to pump 15. If the primary or selected power supply, such as external battery 20 (FIG. 2) or AC mains 45, fails to supply a specified amount of power to pump system 15, reserve battery 10 may be connected to provide power to operate pump system 15. Optionally, controller 5 may include an alarm 104, such as an audio alarm, a visual alarm, or both, that alarms when the power from the primary, secondary, or a combination thereof falls below the threshold.

In an embodiment, external power connections 45A and 45B may be interchangeable with one another for external power and communication. External power connections 45A and 45B may be directly connected to ports 40A and 40B. These external power connections 45A and 45B may be configured in other ways to controller 5. For example, external power connections 45A and 45B may connect directly to controller 5 without ports 40A and 40B, respectively. External power connection 45C to pump 15 may be connect directly to port 35. Alternatively, external power connection 45C may be connected in other ways to controller 5. For example, external power connection 45C may connect directly to controller 5 without port 35.

Referring again to FIG. 1, and in an embodiment, a controller battery 50 may be provided within housing. Controller battery 50 may be configured to power various components of controller 5. For example, these components may include one or more components on printed circuit board 25, such as a switch, an audio display, a visual display 55, or the like. Alarm 10A may be integrated with audio and/or visual display 55. The audio display or visual display 55 may include the alarm 10A as described herein above. In other words, battery 50 may provide power for computing or other electronic functions in contrast to power provided by reserve battery 10 to pump device 15.

Controller 5 with reserve battery 10 may provide emergency power to operate pump 15 in a wide variety of situations. For example, a user may mistakenly choose to use a depleted battery 20 such that battery 20 has no power or inadequate power without a means to recharge battery 20 or to connect to an AC mains. Also for example, a user may plug in a battery backwards, unplug an incorrect battery, or remove AC mains power from powering pump 15. If the user incorrectly operates two power sources of a traditional system, pump 15 will cease to operate. In contrast, controller 5 with reserve battery 10 will not provide a user the opportunity to mistakenly avoid powering pump 15. As such, the user may rely on a single external power source 45A or 45B. If controller 5 determines that pump 5 is receiving no power or inadequate power, reserve batter 10 may be invoked to temporarily provide an adequate amount of power to operate pump 15. In one embodiment, reserve battery 10 has about 30 minutes of power to operate pump 15 if power from the external source, e.g., external power connections 45A and 45B, is removed or inadequate to power pump 15. In other embodiments, the operating time may be about 15 to 20 minutes, or at least 50 minutes, for the reserve battery 10.

With reserve battery 10 contained in controller 5, a patient may operate pump 15 on a single external battery. This allows a patient to carry less weight or extend the amount of operating time by switching between two external battery packs.

It should be appreciated by those skilled in the art and the clinical use of implantable mechanical circulatory support devices that the ability to continue pumping blood for a time with no power applied to the controller is an improvement over currently existing devices.

It should also be appreciated by those skilled in the art that the methods and apparatus having a controlling housing with a reserve battery therein applies equally to mechanical circulatory support devices other than VADs, including 1) left ventricular assist devices, 2) right ventricular assist devices, 3) total artificial hearts (when the native heart is removed), 4) mechanical assist blood pumps that are placed in areas of the circulatory system that do not directly assist the ventricles of the heart.

What is claimed is:

1. A method of providing a reserve power source for a ventricular assist device, the method comprising:
   powering the ventricular assist device with a primary power source, the primary power source including at least one from the group consisting of an external battery and AC mains;
   monitoring power provided to the ventricular assist device by the primary power source; and
   powering the ventricular assist device with a reserve power source disposed within a controller housing when the monitored power is inadequate to run the ventricular assist device, the ventricular assist device being disposed subcutaneously within a patient, the controller housing being disposed externally of the patient and including a first port for connecting to external battery of the primary power source and a second port for connecting to the AC mains of the primary power source, and the ventricular assist device and the controller housing being connected by a percutaneous cable.

2. A method in accordance with claim 1, further comprising operating the ventricular assist device with only two external packages.

3. A method in accordance with claim 1, further comprising providing the primary power source as AC mains.

4. A method in accordance with claim 3, further comprising operating the ventricular assist device with only one external package.

5. A method in accordance with claim 4, further comprising operating the ventricular assist device with only the reserve power source within the controller housing when the monitored power is inadequate to run the ventricular assist device.

6. A method in accordance with claim 1, further comprising:

operating the controller housing using a primary power source with at least one printed circuit board disposed in the housing; monitoring power provided to the ventricular assist device with components on the at least one printed circuit board; switching from the primary power source to a reserve battery disposed in the controller housing to power the ventricular assist device when the power provided by the primary power source is inadequate for the ventricular assist device.

7. A method of providing a reserve power source for a mechanical circulatory support device, the method comprising:

powering the mechanical circulatory support device with a primary power source, the primary power source including at least one from the group consisting of an external battery and AC mains;

monitoring power provided to the mechanical circulatory support device by the primary power source; and powering the mechanical circulatory support device with a reserve power source disposed within a controller housing when the monitored power is inadequate to run the mechanical circulatory support device the mechanical circulatory support device disposed subcutaneously within a patient, the controller housing disposed externally of the patient and including a first port for connecting the external battery of the primary power source and a second port for connecting to the AC mains of the primary power source, and the mechanical circulatory support device and the controller housing connected by a percutaneous cable.

* * * * *